United States Patent [19]

Bruno

[11] Patent Number: 5,031,767
[45] Date of Patent: Jul. 16, 1991

[54] NEEDLE REMOVAL/CONTAINMENT AND TRANSPORT APPARATUS FOR SAFE STORAGE AND DISPOSAL OF HYPODERMIC NEEDLES/SYRINGE ASSEMBLIES

[76] Inventor: John Bruno, 77-83 Second Ave., Paterson, N.J. 07514

[21] Appl. No.: 423,977

[22] Filed: Oct. 19, 1989

[51] Int. Cl.⁵ .............................................. B65D 83/10
[52] U.S. Cl. .................................... 206/370; 206/366; 220/404; 220/908; 229/907
[58] Field of Search ............... 206/364, 365, 366, 370; 220/403, 404, 908; 229/907

[56] References Cited

U.S. PATENT DOCUMENTS

| | | | |
|---|---|---|---|
| 2,757,859 | 8/1956 | Holland | 220/404 |
| 4,375,849 | 3/1983 | Hanifl . | |
| 4,534,489 | 8/1985 | Bartlett | 220/908 |
| 4,603,791 | 8/1986 | Spierer et al. | 220/404 |
| 4,662,516 | 5/1987 | Baker, Sr. et al. | 206/370 |
| 4,667,821 | 5/1987 | Shillington | 206/366 |
| 4,674,676 | 6/1987 | Sandel et al. | 206/366 |
| 4,702,385 | 10/1987 | Shillington et al. | 220/908 |
| 4,738,362 | 4/1988 | Burns et al. | 206/366 |
| 4,846,397 | 7/1989 | Copeland | 206/366 |
| 4,863,052 | 9/1989 | Lambert | 220/908 |

Primary Examiner—David T. Fidei
Attorney, Agent, or Firm—Morgan & Finnegan

[57] ABSTRACT

A needle removal/containment and transport apparatus for potentially injurious medical implements, generally comprising a storage and transport housing; a storage container slidably inserted within the housing for receiving and storing the implements; a plastic bag surrounding the container; a needle removal device mounted on the container for threadably disengaging needle/syringe assemblies and depositing the needles into the container; and an entry port formed on the container with a releasably insertable plug member for depositing implements such as syringes, scalpels, etc. into the container. The housing is formed with flap members to permanently seal the container within the housing, yet permit access to the container. The housing is further formed with a cover member to permanently sealingly close the housing for transport to ultimate disposal. The needle removal device comprises a plate member formed with a first receiving slot, and an integral needle engaging member comprising a pair of opposed finger members integrated with a base member to form a stepped slot providing a second receiving slot and a contiguous engaging slot. The first receiving slot is laterally aligned with the second receiving slot at an elevation generally higher with respect thereto. The needle hub is slidably translated through the second receiving slot into engagement with the needle removal device via the engaging slot whereupon the syringe can be rotated relative to the needle hub to unthread the needle from the syringe. The unthreaded needle and syringe are then removed from the engaging slot and translated through the second receiving slot and into the first receiving slot such that the needle hub is disposed on the underside of the plate member permitting the needle to drop into the container. In the event the needle has not been fully unthreaded from the syringe or in the case of a multi-sample needle where the needle can hang-up within the syringe, the needle hub will engage the underside of the plate member in response to upward forces applied to the syringe to act as a stop preventing the needle from being pulled out of the removal device.

31 Claims, 8 Drawing Sheets

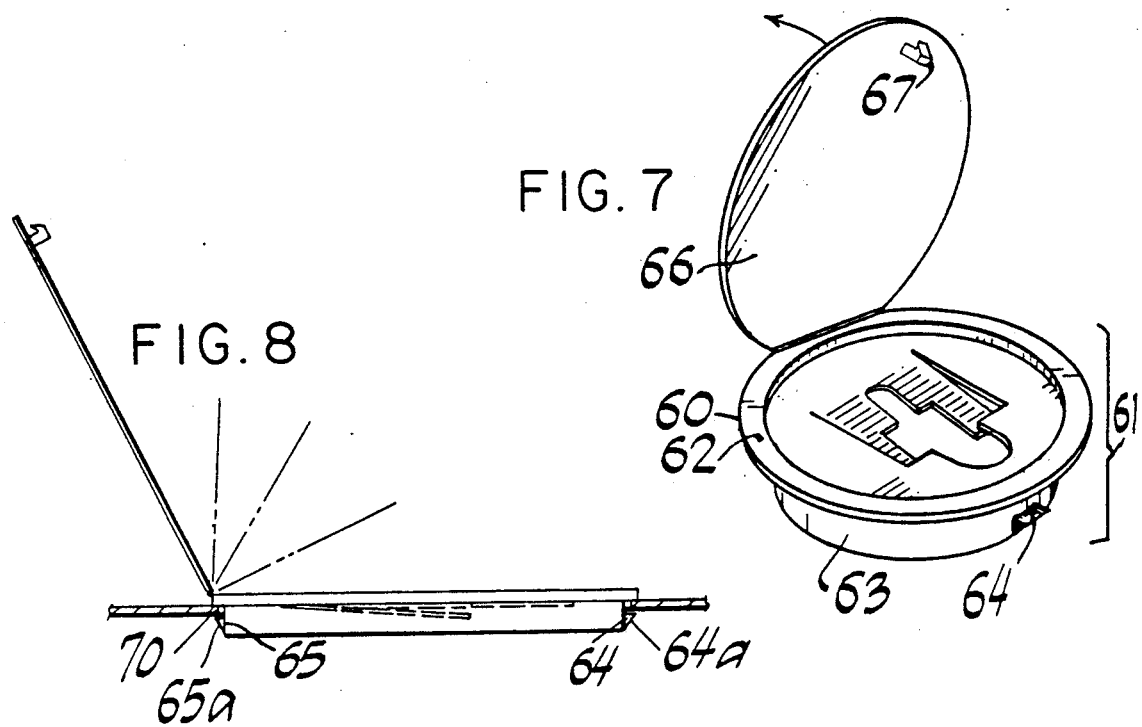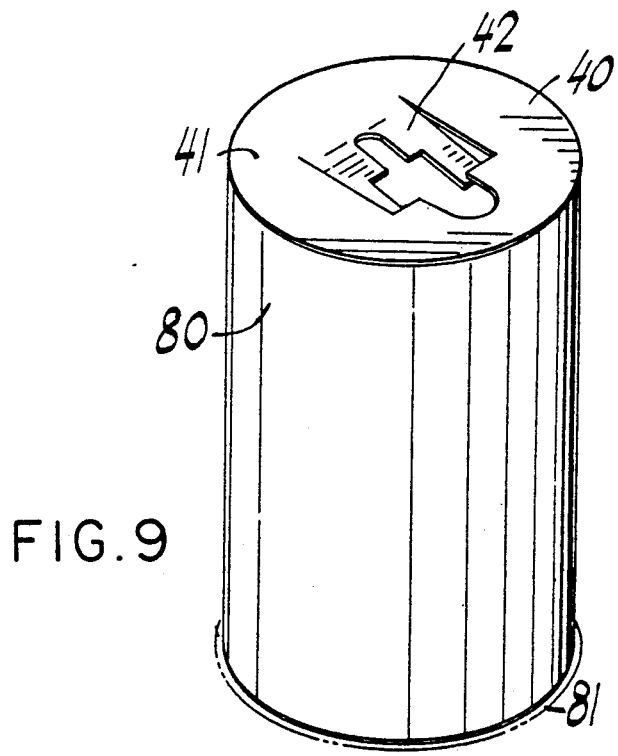

NEEDLE REMOVAL/CONTAINMENT AND TRANSPORT APPARATUS FOR SAFE STORAGE AND DISPOSAL OF HYPODERMIC NEEDLES/SYRINGE ASSEMBLIES

BACKGROUND AND OBJECTS OF THE INVENTION

The present invention relates generally to devices for safely disassembling, collecting and storing the needle and syringe portions of hypodermic needle/syringe assemblies and, more particularly, to a needle removal/-containment and transport apparatus for the safe detachment, storage and ultimate disposal of such implements, as well as other potentially injurious or contaminated implements such as used scalpel blades, and the like, which pose a risk of causing infection or even disease by exposure to such implements.

With the advent of disposable medical implements such as surgical tools, hypodermic needles, scalpel blades and other sharp implements, a need has developed for ways to safely store, and safely handle for disposal, such implements after use without risk of exposing people to injury, infection or disease by improper handling, until proper disposal can be made. The tragic outbreak of the highly contagious AIDS disease has dramatically highlighted the need for safer handling, storage and disposal of such implements.

In the case of disposable hypodermic needles, it had been common practice to break or cut the needles prior to discarding the needle and syringe in order to reduce the size of the overall needle/syringe device and to eliminate the sharp point from the needle to reduce the risk of injury which might otherwise result from handling. In breaking or cutting the needles, however, a substantial danger exists of accidental puncture during the breaking or cutting operation, thus exposing the holder to possible injury and, further, to possible infection or disease as a result of such puncture. In addition, any residual medication in the needle can splatter onto the person or his clothes and there is a further danger that potentially harmful fumes can be inhaled. The blades of the cutting tool also become a breeding ground for germs, bacteria and other disease-causing micro-organisms to which the unsuspecting person cutting the needle is unnecessarily exposed.

Recently, an even greater danger has been recognized in connection with the handling and dismantling of used needles and other sharp medical implements. It is now recognized that certain diseases, most notably Hepatitis B, can be transmitted by covert percutaneous—i.e., by merely contacting the contaminated needle or implement.

As a result of the foregoing dangers, the preferred current practice is to dispose of such devices intact, without dismantling them. Often, hypodermic needles are re-capped after use with the protective sheaths used during shipment from the manufacturer, in order to prevent injury while carrying the device to a suitable disposal unit. This practice itself, however, often results in puncture wounds suffered while re-capping the needle point. Because of this danger, it is now recommended that needles not be re-sheathed after use.

In response to the foregoing dangers, various proposals have been advanced for eliminating some of the risks involved in the handling, storage, and disposal of hypodermic needles and other sharp medical implements, including (1) devices capable of removing the needle from its syringe after use and safely storing it for ultimate disposal, as identified, for example, in my U.S. Pat. No. 4,801,013, and (2) specially designed containers for storing the used implements, including some made of all plastic, as identified, for example, in my pending patent application Ser. No. 344,466.

Even with the advantages achieved by my previous containers and needle removal device, however, there is still a need for continued improvement in safety and economy in the medical waste disposal industry, especially with regard to high volume medical waste generators such as hospitals. For example, although my previously discussed needle removal device overcomes virtually all of the aforesaid dangers, it is relatively compact in size to facilitate easy transport on the person of the user and requires being deposited in another larger storage container for transport to ultimate disposal.

Although my previously mentioned containers also overcome virtually all of the aforesaid dangers associated with the use and disposal of needle/syringe devices, they too have certain limitations. For example, plastic containers may be susceptible to breaking or shattering if inadvertently dropped, especially after prolonged exposure to extreme cold. Moreover, containers made from injection molded plastics become excessively expensive when manufactured in larger sizes. The cost of the injection mold alone for containers having volumes of 5 gallons or greater has discouraged manufacturers from making such containers. Even the manufacturing cost of non-injection molded plastic containers increases tremendously with increasing container volume.

Accordingly, it is an object of the present invention to provide a new and improved storage receptacle and transport apparatus for the storage and disposal of hypodermic needles, syringes, scalpels and other sharp or pointed implements which pose a health risk by reason of injury, puncture or even mere contact. It is another object of the present invention to provide a new and improved storage receptacle and transport apparatus for such potentially injurious implements, wherein the receptacle is resistant to cracking, shattering and puncture by the implements retained therein, and wherein the transport apparatus permits convenient and complete disposal of the implements together with the receptacle.

It is yet a further object of the present invention to provide a new and improved storage receptacle and transport apparatus for potentially injurious implements, which is compact, lightweight, and can be conveniently transported from place to place as well as transported to ultimate disposal even when the receptacle is filled to capacity with the used implements. It is also an object of the invention to provide a new and improved storage receptacle and transport apparatus for storage and disposal of potentially injurious implements, which is adapted for use by high volume medical waste generators, thus eliminating the need for a separate larger storage receptacle.

It is still another object of the invention to provide a new and improved storage receptacle and transport apparatus for potentially injurious implements, which includes a new and improved needle removal device adapted to detach hypodermic needles threadably engaged to a syringe body via a needle hub member by fixedly engaging the hub member, and deposit them into the storage receptacle while substantially preventing contaminating contact between the used needle and the user of the device.

It is still another object of the invention to provide a new and improved needle removal device which is adapted to insure complete disengagement between the needle and syringe portions of hypodermic needle/syringe assemblies in the event the user fails to completely threadably disengage the needle and syringe when using the device, or, in the case of multi-sample needles, where the needle portion disposed within the syringe causes the needle to "hang-up" in the syringe.

It is still another object of the invention to provide a new and improved storage receptacle and transport apparatus for storing potentially injurious implements, wherein the used syringe devices (as well as other implements) can be conveniently and safely deposited into the receptacle after disengagement from the corresponding needles. It is yet another object of the invention to provide such a storage receptacle and transport apparatus which facilitates a person's ability to easily recognize when the receptacle has been filled to its intended capacity.

It is another object of the invention to provide such a new and improved storage receptacle and transport apparatus wherein the implements are received and stored in a drum-type container made from a substantially rigid fibreboard material and wherein the container is placed within a corrugated paperboard housing which is permanently sealable such that the entire device can be conveniently transported to ultimate disposal. In addition, it is an object of the invention to provide a plastic bag surrounding the container within the housing to provide a triple layer of protection against potential contaminating contact with the implements stored within the container.

The foregoing specific objects and advantages of the invention are illustrative of those which can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variations which may be apparent to those skilled in the art. Accordingly, the present invention resides in the novel parts, constructions, arrangements, combinations and improvements herein shown and described.

SUMMARY OF THE INVENTION

Briefly described, the present invention comprises a needle removal/containment and transport apparatus for safe storage and disposal of hypodermic needle/syringe assemblies and other potentially injurious medical implements, generally comprising (1) a corrugated paperboard storage and transport housing; (2) a substantially rigid fibreboard storage container slidably inserted within the housing for receiving and storing the implements; (3) a plastic bag surrounding the container to catch and retain any residual liquid which may remain in the used implements and which may leak through the container; (4) a needle removal device mounted on the container for threadably disengaging hypodermic needle/syringe assemblies and depositing the needles into the container; and (5) entry means formed on the container with releasably insertable plug means for depositing implements such as syringes, scalpels, etc. into the container.

Accordingly to one specific aspect of the invention, the storage and transport housing is formed in a generally rectangular configuration, and is provided with a pair of carrying handles defined by slots within the housing sidewalls so that the housing can be easily moved from place to place. To secure the container within the housing after the container has been filled to capacity with the used implements, the housing is provided with a cover member flexibly connected to the upper horizontal edge of the rear facing sidewall thereof in hinge-like fashion. The cover comprises a base portion proportioned to completely cover the housing opening, and a flap portion which extends from the front edge of the base portion and is flexibly connected thereto in hinge-like fashion.

As preferably embodied, the housing cover flap is formed with a pair of opposed projecting tabs which are slidably frictionally inserted into a pair of receiving slots formed in the front sidewall of the housing to secure the cover over the housing opening. Also, the inside of the flap is provided with adhesive strips which can be pressed against the front sidewall of the housing to adhere the flap to the sidewall. Advantageously, the rear sidewall of the housing is formed with a pair of receiving slots which are proportioned similarly to the slots in the front sidewall. The hinge-like connections between the cover and rear sidewall of the housing, and between the cover and the cover flap, allow the cover to be bent backwards and the flap bent inwardly towards the rear sidewall so that the projecting tabs can be frictionally inserted into the rear sidewall slots to secure the cover to the housing, out of the way of the container when the container is in use.

To effectively permanently seal the container within the housing, the housing is preferably provided with a pair of protective flaps flexibly connected in hinge-like fashion to the two sidewalls of the housing connecting the front and rear sidewalls. As here embodied, each flap is formed with an arm member flexibly connected in hinge-like fashion to one of the connecting sidewalls, and a base member flexibly connected in hinge-like fashion to the corresponding arm member. Each base member is proportioned to essentially the size of the housing opening and is provided with a square opening therewithin generally smaller in size than the housing opening. The flexible connections between the arm members and their respective sidewall members and between the base members and their respective arm members allow the protective flaps to be folded into the housing opening, one over the other, to align the openings and permit access to the container therethrough. The openings in the protective flaps are proportioned relative to the housing opening so as to permit normal operation of the needle removal device and plug member (described below), and such that the edges of the base members defining the flap openings provide a protective lip over any portions of the housing opening left exposed after the container is placed therewithin. To seal the container within the housing, the flaps are glued together upon being folded into the housing, or can be formed with adhesive strips to adhere one to the other.

According to another specific aspect of the invention, the container comprises a body member having an open end and a closed end and a cover releasably retained over the body. For ease and economy of fabrication, and to facilitate easy and safe transport of the needle/- removal containment device, the container preferably has about a six gallon capacity which can hold about 1,000 multi-sample needles. The container cover is formed with an entry port provided with a releasably insertable plug device for purposes of depositing used syringes, scalpels and the like into the container for disposal. As preferably embodied, the plug device comprises a plug body providing a flange member, a shaft member connected to the plug body, and a knob connected to the shaft member. The flange, which is generally wider than the entry port in the cover, acts as a stop to prevent the plug from falling into the container. To prevent the plug from being inadvertantly detached from the container, a generally L-shaped retaining wire is provided which is connected to the plug shaft via a hooked end portion and is formed with a cork-screw-like end portion at the free end thereof. The cork-screw-like end portion is inserted into the container via a small eyelet opening in the container cover. The L-shaped configuration of the wire allows the plug to pivot about the entry port, while the cork-screw end portion of the wire prevents the wire from being removed from the eyelet opening while the plug is being handled by the user.

According to another aspect of the invention, a needle removal device is fixedly attached to the container cover over an opening formed in the cover for purposes of safely removing used needles from multi-sample and single sample needle syringe devices and depositing them into the container. As here embodied, the needle removal device comprises a disc-like plate member formed with a generally U-shaped receiving slot and an integral needle hub engaging member canted downwardly from the plate member into the container. The needle hub engaging member comprises a base portion formed integrally with a pair of opposed finger members. The base portion and finger members define a stepped needle receiving/engaging slot comprising a generally rectangular shaped slot portion and a generally U-shaped slot portion formed contiguous therewith. According to the invention, the base member slot and the U-shaped slot portion of the needle receiving/engaging slot are dimensioned so that the needle hub collars of most conventional multi-sample and single sample needle/syringe assemblies can be easily slidably received therewithin and extracted therefrom. Moreover, and as preferably embodied, the rectangular shaped slot portion of the needle receiving/engaging slot is dimensioned such that the edges of engaging member 42 forming the slot can frictionally engage the needle hub to hold the needle/syringe device in place and thereby facilitate the disengaging process between the needle and syringe.

To operate the needle removal device, a needle/syringe assembly is inserted into the rectangular portion of the needle receiving/engaging slot, needle end first, so that the needle passes through the slot into the container and the disc member formed on the needle hub rests on the finger members. By application of light finger pressure by the user, the needle/syringe device is slid through the needle receiving/engaging slot until the needle hub is frictionally engaged within the U-shaped portion thereof. The user then rotates the syringe counterclockwise to unthread the syringe from the needle hub. The user next applies light finger pressure to the syringe to disengage the needle hub from the U-shaped slot portion and slide the needle back through the rectangular slot portion and into the plate member slot. The inwardly canted surface of the needle hub engaging member relative to the plate member causes the entire needle hub, including the disc member, to slide under the edges of the plate member which define the plate member slot, and thereby permit the needle to drop into the container. Because the diameter of the needle hub disc is larger than the width of the plate member slot, the disc acts as an obstructing collar when the syringe is raised upwardly to prevent the needle from being accidently removed from the slot in the event the needle hub has not been fully unthreaded from the collar, or, in the case of multi-sample needles, in the event that the rubber cover conventionally provided over the needle portion within the syringe causes the needle to "hang-up" in the collector.

According to another aspect of the invention, the needle removal/containment and transport apparatus is provided with means for insuring that residual liquid that may remain in a used needle or syringe deposited in the container does not leak through the container and the housing. As here embodied, the container is placed within a plastic bag prior to placement of the container within the housing. The top end of the bag is pulled through the openings in the protective flaps of the housing and draped over the top of the housing's sidewalls. When the apparatus is ready to be transported to disposal, the portions of the bag overlapping the housing's sidewalls are gathered up and tied together with a twist-tie device. The housing cover can then be secured closed over the housing as described above, and the entire device transported to disposal.

It will be appreciated by those skilled in the art that the foregoing brief description and the following detailed description are exemplary and explanatory of the present invention, but are not intended to be restrictive thereof or limiting of the advantages which can be achieved by the invention. Thus, the accompanying drawings, referred to herein and constituting a part thereof, illustrate preferred embodiments of the invention and, together with the detailed description, serve to explain the principles of the invention.

BRIEF DESCRIPTION OF THE DRAWINGS

FIG. 7 is a isometric view showing an alternative embodiment of the needle removal device of FIGS. 1 and 5.

FIG. 8 is a side view of the needle removal device of FIG. 7.

FIG. 9 is a perspective view of a further alternative embodiment of the needle removal device of FIGS. 1 and 5.

DETAILED DESCRIPTION OF PREFERRED EMBODIMENTS

Figure 1:
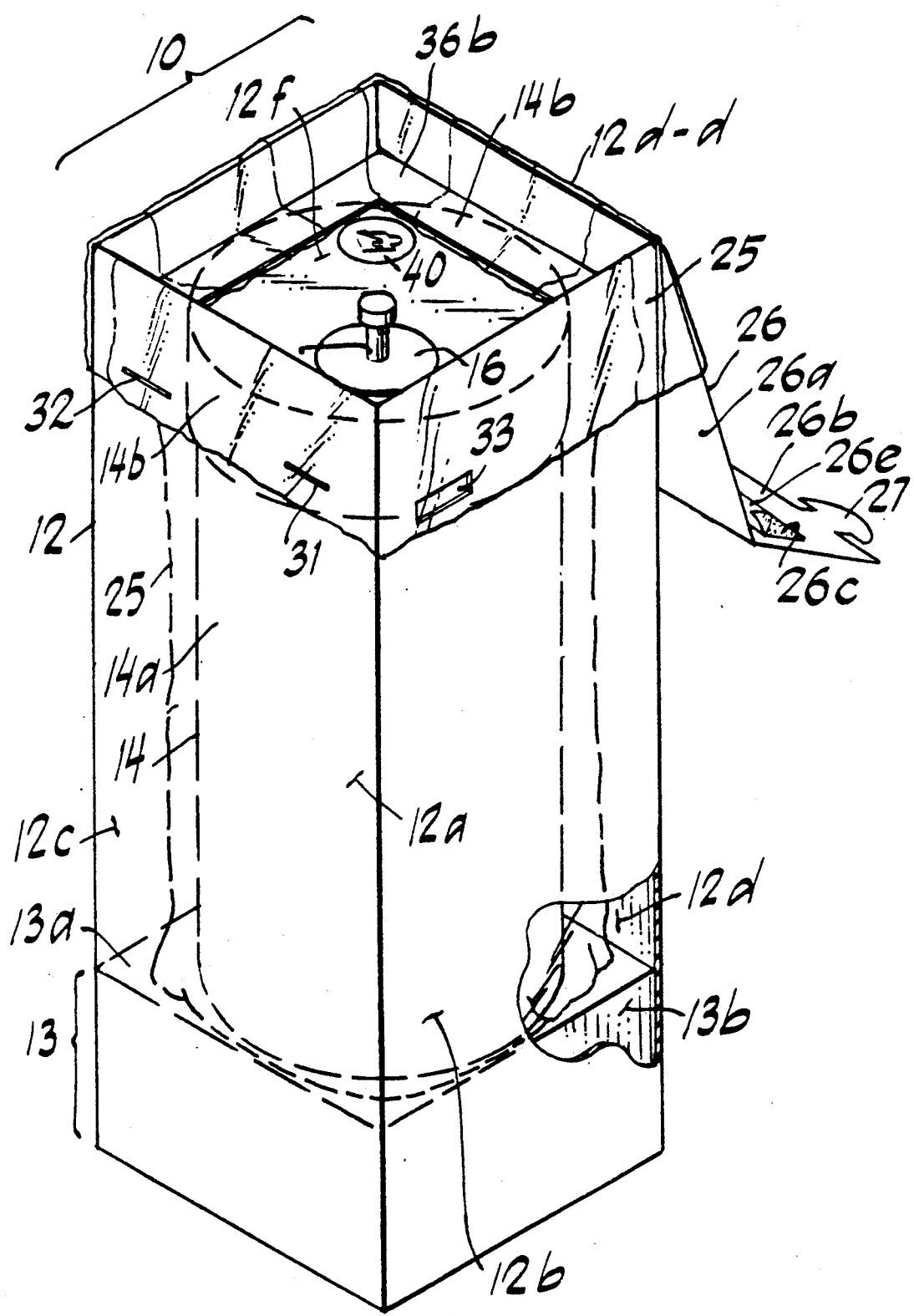
FIG. 1 is an isometric view of a preferred embodiment of the needle removal/containment and transport apparatus of the present invention.
Figure 1A:
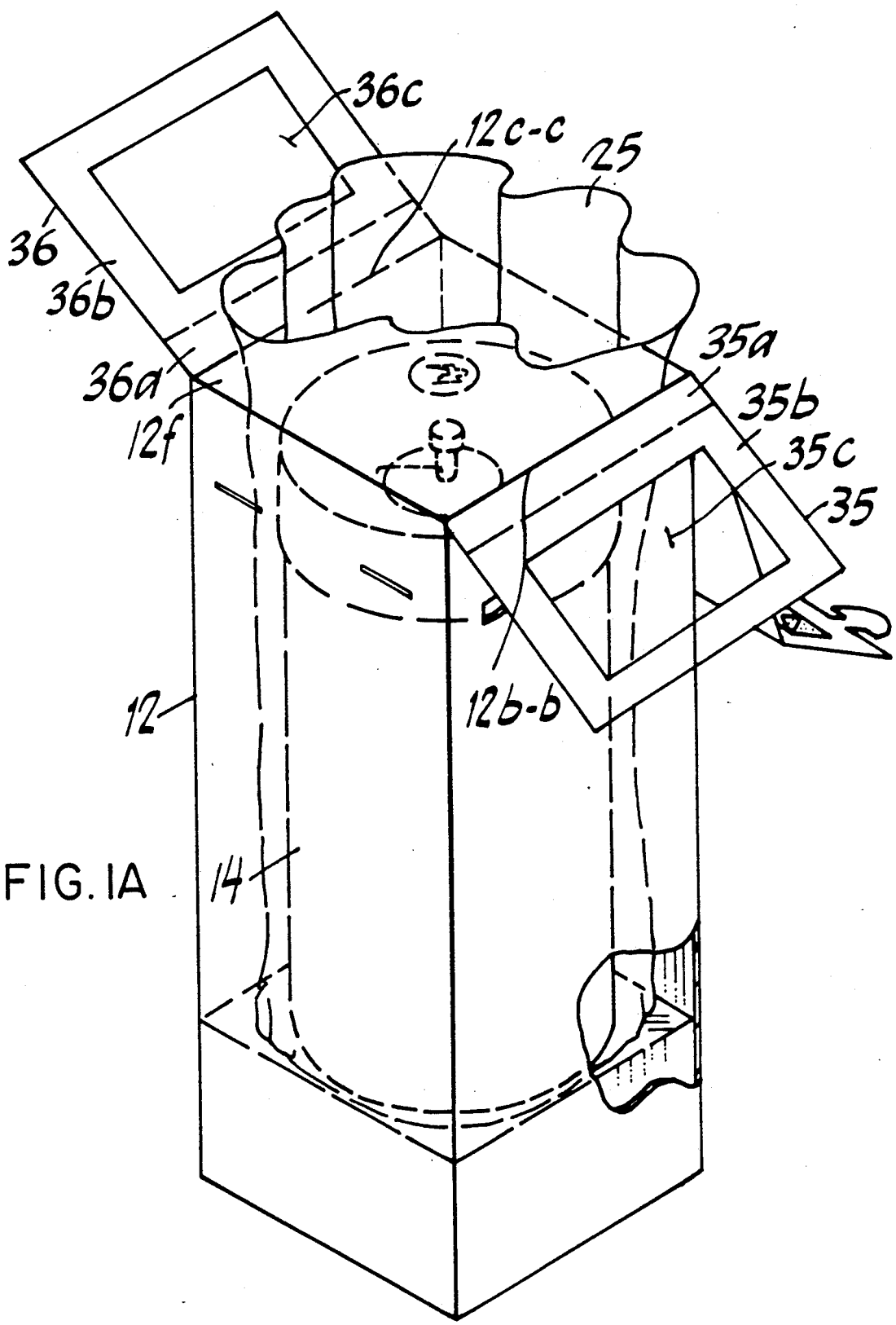
FIG. 1A is an isometric view of the apparatus of FIG. 2 showing the protective cover flaps for the transport housing of the invention.

Referring now to the accompanying drawings wherein like reference characters refer to like parts throughout the various views, there is shown in FIGS. 1-9 the preferred embodiments of the needle removal/-containment and transport apparatus for potentially injurious medical implements (indicated generally at 10) of the present invention. As herein embodied, apparatus 10 generally comprises (1) a storage and transport housing 12, (2) a storage container 14 slidably inserted within housing 12 for receiving and storing used medical implements, (3) a plastic bag 25 surrounding container 14 to catch and retain any residual liquid which may remain in the used implements and which may leak through the container, (4) a needle removal device 40 mounted on container 14 for removing used single or multi-sample needles from their syringes and depositing them into the container, and (5) an entry port 14b formed on container 14 and provided with a releasably insertable plug device 16 for depositing syringes, scalpels, etc., into the container.

According to the invention, housing 12 is formed in a generally rectangular configuration, comprising sidewall members 12a, 12b, 12c and 12d, and bottom wall member 12e, which are structurally integrated to form an opening 12f at the top end of the housing. As preferably embodied, housing 12 is constructed from a lightweight, corrugated paperboard material having a sidewall and bottom wall thickness of at least about ⅛ inch. The housing is provided with a pair of carrying handles defined by slots 33 and 34 formed in sidewall 12b and 12c, respectively, so that the housing can be easily moved from place to place. As here embodied, housing 12 may, for example, be a stand-alone paperboard carton of the type manufactured by Greis Bros. Corporation.

Advantageously, housing 12 is proportioned to an overall height of about 26½ inches, which enables it to accommodate the height of fibreboard containers preferably used in the practice of the invention (see discussion below) ranging in capacity from 1 to 55 gallons, and which will be a comfortable height for most users. Of course, the size of housing opening 12f will vary in accordance with the volume of container 14. (For example, for a 6 gallon container, opening 12f should preferably be about 11⅝ inches square). For containers having a capacity of 12 gallons or less, the same overall height of housing 12 can be maintained by gluing a false bottom 13 into the housing, formed from a base 13a and two sidepanels 13b, upon which the container can sit. (It will be understood by those skilled in the art that commercial fibreboard drums having capacities between 1 and 12 gallons are manufactured with generally equivalent heights).

To secure housing 12 closed for transport to disposal after container 14 has been filled to capacity with the used medical implements, housing 12 is provided with a cover 26 flexibly connected to the upper horizontal edge 12d—d of sidewall 12d in hinge-like fashion. As here embodied, cover 26 comprises a base portion 26a proportioned to completely cover opening 12f in housing 12, and a flap portion 26b which extends from the front edge of base 26a and is flexibly connected thereto in hinge-like fashion. Flap 26b is formed with a pair of opposed projecting tabs 27 and 28, which can be slidably frictionally inserted into receiving slots 31 and 32, the cover over opening 12f.

To further secure cover 26 over opening 12f, the back of flap 26b is provided with a pair of generally rectangular adhesive strips 26c and 26d, each covered by a removable tape 26e. Adhesive strip 26c is preferably located at about the center of flap 26b and adhesive strip 26d is preferably formed over the hinge-like connection between the flap and cover 26. When the tape is removed from strips 26c and 26d, the strips can be pressed against sidewall 12a by finger pressure applied to the front of flap 26b to adhere the flap to the sidewall. As preferably embodied, sidewall 12d is formed with receiving slots 29 and 30 which are proportioned similarly to slots 31 and 32. The hinge-like connections between cover 26 and sidewall 12d of housing 12, and between flap 26b and cover 26, allow the cover to be bent backward, and flap 26b to be bent inwardly toward sidewall 12d, so that tabs 27 and 28 can be frictionally inserted into slots 29 and 30, respectively, to secure the cover to the housing, out of the way of the container when the container is in use.

To effectively permanently seal container 14 inside housing 12, the housing is preferably provided with a pair of protective flaps 35 and 36. As here embodied, each flap is formed with an arm member (35a, 36a) flexibly connected in hinge-like fashion to horizontal upper edges 12b-b and 12c-c of sidewalls 12b and 12c, respectively, and a base member (35b, 36b) of generally square configuration flexibly connected in hinge-like fashion to the corresponding arm member. According to the invention, each base member (35, 36) is proportioned to essentially the size of opening 12f, and is provided with a square opening therewithin (35c and 36c) generally smaller in size than opening 12f. The flexible connections between arm members 35a, 36a and their respective sidewall members, and between base members 35b, 36b and their respective arm members, allow the protective flaps to be folded into opening 12f of housing 12, one over the other, to align openings 35c, 36c and permit access to container 14 through the aligned openings. Openings 35c, 36c are proportioned relative to opening 12f so as to permit normal operation of plug member 16 and needle removal device 40 (described in detail below), and such that the edges of base members 35, 36 forming the respective openings 35c, 36c provide a protective lip over any portions of opening 12f left exposed after container 14 is placed therewithin. To seal container 14 inside housing 12, flaps 35, 36 are preferably glued together when folded into the housing. Alternatively, the flaps may each be provided with adhesive strips (not shown) along the bottom surfaces thereof so that they can be adhered together when folded inside housing 12.

To collect the used medical implements, the present invention further provides, as preferably embodied, a drum-type container 14 constructed from a substantially rigid fibreboard material, which may be, for example, of the type manufactured by Foremost Corrugated Company, Inc. As here embodied, container 14 is slidably insertable within housing 12 through opening 12f and comprises a body member 14a having an open end and a closed end and a cover 14b releasably retained over the body. Although any size and configuration drum-type container may be used in the practice of the invention, it will be understood by those skilled in the art that fibreboard drums, which are most preferred, generally have either a circular or square open end and are most readily commercially available in sizes up to 55 gallons. For ease and economy of fabrication, and to facilitate easy and safe transport of device 10 to ultimate disposal when container 14 is full, it is preferred that the container have about a 6 gallon capacity (which as those skilled in the art will readily understand can hold about 1000 multi-sample needles), with about a 10 inch diameter, and a height of about 19½ inches.

To safely remove used needles from multi-sample and single sample needle/syringe devices and deposit the needles into container 14, the present invention provides a needle removal device 40 fixedly attached to cover 14b over an entry port 14c formed in the cover. As here embodied, needle removal device 40 comprises a disc-like plate member 41 formed with a generally U-shaped receiving slot 43, and an integral needle hub engaging member 42 canted downwardly from plate member 41 so as to communicate with the interior of container 14. Needle hub engaging member 42 comprises a base portion 42a formed integrally with a pair of opposed finger members 42b and 42c. Base 42a and finger members 42b and 42c define a stepped needle receiving and engaging slot 44 comprising a generally rectangular shaped slot portion 44a and a generally U-shaped slot portion 44b formed contiguous therewith.

Figure 5:
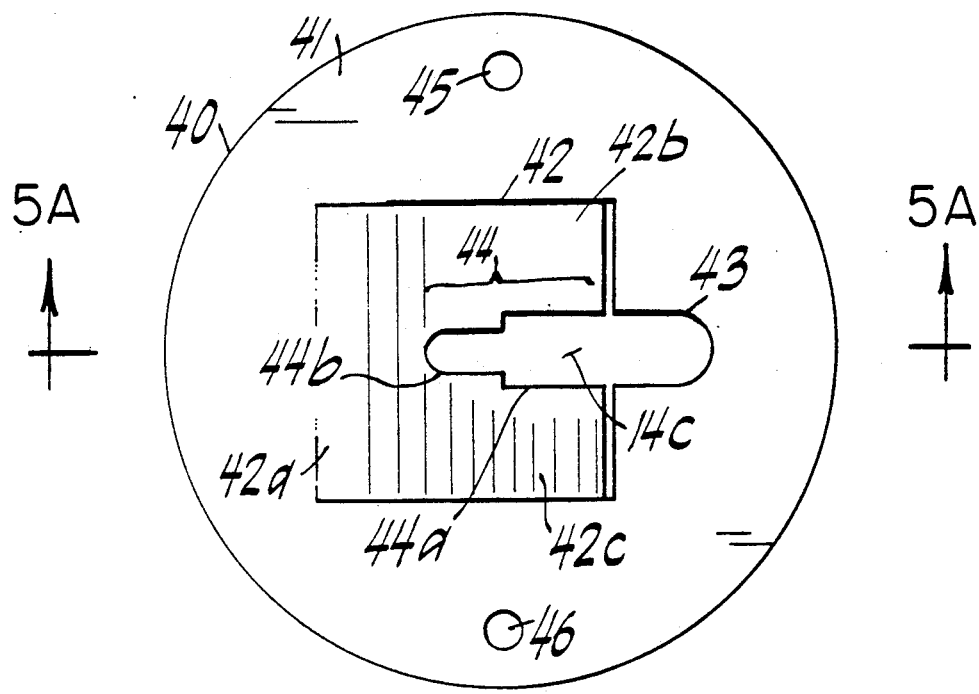
FIG. 5 is a top view of a preferred embodiment of the needle removal device of the present invention.

As here embodied, needle removal device 40 is preferably fabricated from an injected molded thermo-plastic material but can be fabricated from other materials as desired, including being stamped into a piece of metal such as tin, aluminum, or the like. Moreover, the needle removal device can be attached to cover 14b of container 14 in any conventional manner to ensure a secure attachment which will not loosen during long periods of use. For example, as shown in FIG. 5, plate member 41 can be formed with holes 45 and 46 for attachment to cover 14 via rivet-type connection or other suitable fastener.

According to the invention, slots 43 and 44a of device 40 are preferably dimensioned to a width of about 0.200 inches and a length of about 0.250 inches so that the needle hub collars of most conventional multi-sample and single sample needle/syringe assemblies can be easily slidably received therewithin and extracted therefrom. Also, as preferably embodied, slot 44b is dimensioned to a length of about 0.250 inches and a width of about 0.150 inches to slidably receive the needle hubs and such that the edges of engaging member 42 forming the slot 44b frictionally engage the needle hub to hold the needle/syringe device in place and thereby facilitate the disengaging process between the needle and syringe (fully described below). Advantageously, and as preferably embodied, the entire device 40 is of a relatively compact size, having an overall diameter of 2.25 inches. It should be clear to those skilled in the art that the circular disc configuration of device 40 depicted in the drawings should not be limiting of the invention. For example, device 40 can be fabricated with a square, rectangular or other suitable configuration with no effect on the operation of the device.

Figure 6:
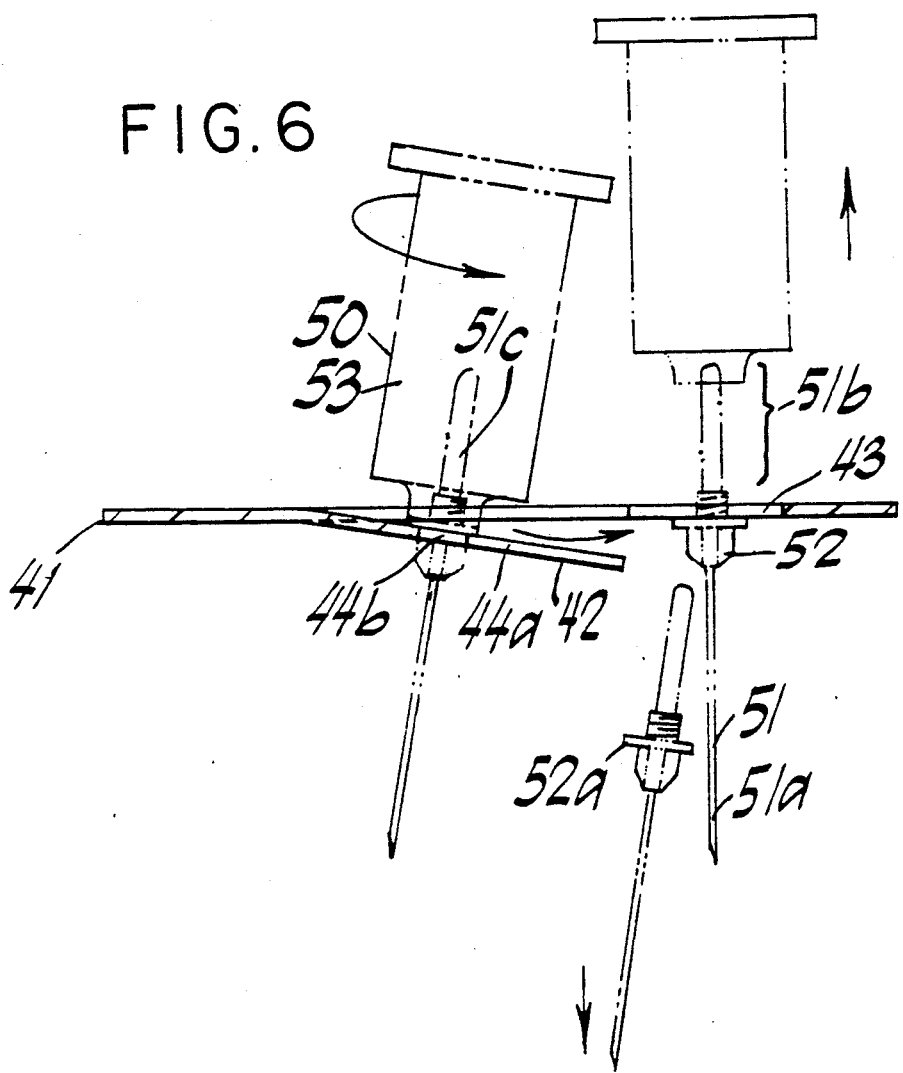
FIG. 6 is a side view through Section 5A—5A showing operation of the needle removal device of FIG. 5.

Operation of needle removal device 40 is straightforward. FIG. 6 illustrates the operation of needle removal device 40 for a conventional multi-sample needle/syringe assembly 50 comprising a vacuum tube collector-type syringe body 53 threadably engaged with the needle hub 52 of a multi-sample needle member 51. Needle 51 is formed with a first portion 51a exiting syringe 53 and a second portion 51b located within the syringe and provided with a rubber cover 51c. (The operation of device 40 with respect to conventional threaded single sample needle/syringe assemblies is identical). According to the invention, needle/syringe assembly 50 is inserted into slot 44a of device 40 until portion 51a of needle 51 passes through the slot and into container 14 and disc member 52a formed on the needle hub rests on finger members 42a and 42b (as here embodied, the diameter of disc 52a will generally be larger than the width of both slots 44a and 44b). By the application of light finger pressure, assembly 50 is next slid through slot 44a and into slot 44b such that hub 52 is frictionally engaged by the edges of member 42 defining slot 44b, and held in place within the slot.

At this point, the user rotates syringe 53 counterclockwise to unthread the syringe from the needle hub. Because the diameter of disc 52a is larger than the width of slot 44b, the disc acts as a stop to prevent disengagement of hub 52 from slot 44b due to downward forces which may be applied when unthreading the hub and syringe. Although unthreaded from the needle hub, the syringe at this point is not fully disengaged from the needle. Rather, the user next applies light finger pressure to syringe 53 to disengage needle hub 52 from slot 44b and slide the needle back through slot 44a and into slot 43. The inwardly canted surface of needle engaging member 42 relative to plate member 41 causes the entire needle hub 52, including disc member 52a, to slide under the edges of plate member 41 which define slot 43. In this position, needle 51 can safely drop into container 14. Like its relationship with slot 44, disc 52a is larger in diameter than the width of slot 43. Thus, disc 52a acts as an obstructing collar in response to upward forces applied to syringe 53 to prevent the needle from being accidently removed from slot 43 in the event the hub has not been fully unthreaded from the syringe, or in the event that the rubber cover 51c on needle portion 51b causes the needle to "hang-up" in the syringe. If the hub and syringe have not been fully unthreaded, they can be translated back into slot 44 to re-engage the hub with slot portion 44b.

Figure 5A:
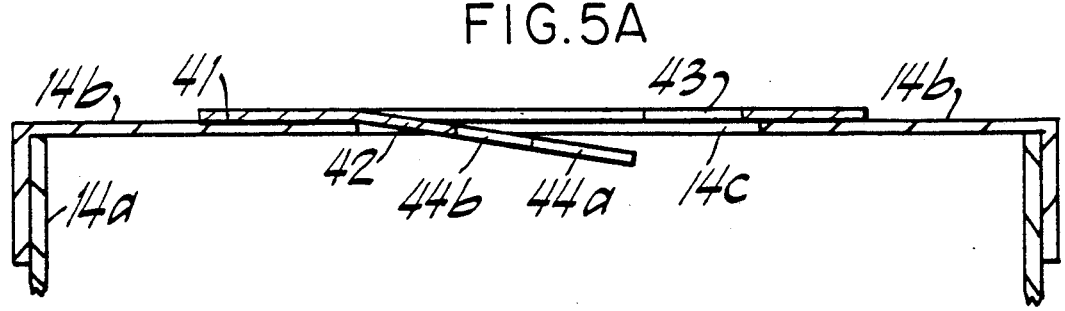
FIG. 5A is a side view through Section 5A—5A of the needle removal device shown in FIG. 5.
Figure 6A:
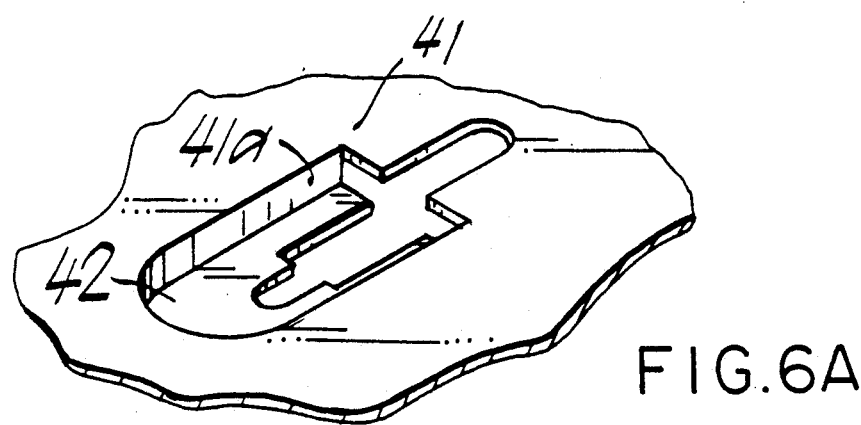
FIG. 6A is an isometric view of an alternative embodiment of the needle removal device of FIG. 5.

Referring now to FIGS. 6A, 7, 8, and 9, there are shown alternate embodiments of the needle removal device of the present invention. As shown in FIG. 6A, by providing a U-shaped sidewall 41a disposed downwardly through plate member 41 to connect needle engaging member 42 to the plate member, the needle engaging member can be recessed into plate member 41 in parallel therewith. In operation, this embodiment of needle removal device 40 functions exactly the same as the embodiment described above and illustrated in FIGS. 5, 5A and 6.

As shown in FIGS. 7 and 8, device 40 can be fabricated as a needle removal insert 60 for insertion in any conventional can or container. As here embodied, device 40 is recessed into a flange member 61, which is fabricated from a resiliently yieldable plastic material and comprises an integral lip member 62 and collar member 63. Collar member 63 is formed with a pair of snap-in tabs 64 and 65 which project therefrom. As here embodied, lip 61 is integrated with a cover member 66 so as to form a "living hinge" connection therebetween. According to the invention, insert 60 is forced into a circular opening 70 formed in a can or container which is slightly smaller in diameter than collar 63 measured across the projecting length of snap-in tabs 64 and 65. As here embodied, the insertion force exerted on insert 60 will cause the canted surfaces 64a and 64b of tabs 64 and 65 to bear upon the edges of the container defining opening 70. This in turn will cause the collar 63 to resiliently yield inward and slide into opening 70. When the container is filled with used needles and ready for disposal, cover 66 is placed over flange 61, pressed downward, and snapingly engaged therewith via a locking member 67 formed on the cover.

As shown in FIG. 9, the needle removal device 40 can also be stamped into the top of a metal can 80. A reversible lid 81, preferably fabricated from a lightweight, flexible plastic, is placed over the bottom of the can when the needle removal device is in use. When the can is filled to capacity and ready for disposal, the lid is removed from the can bottom and fitted over the top of the can to cover the needle removal device.

Figure 2:
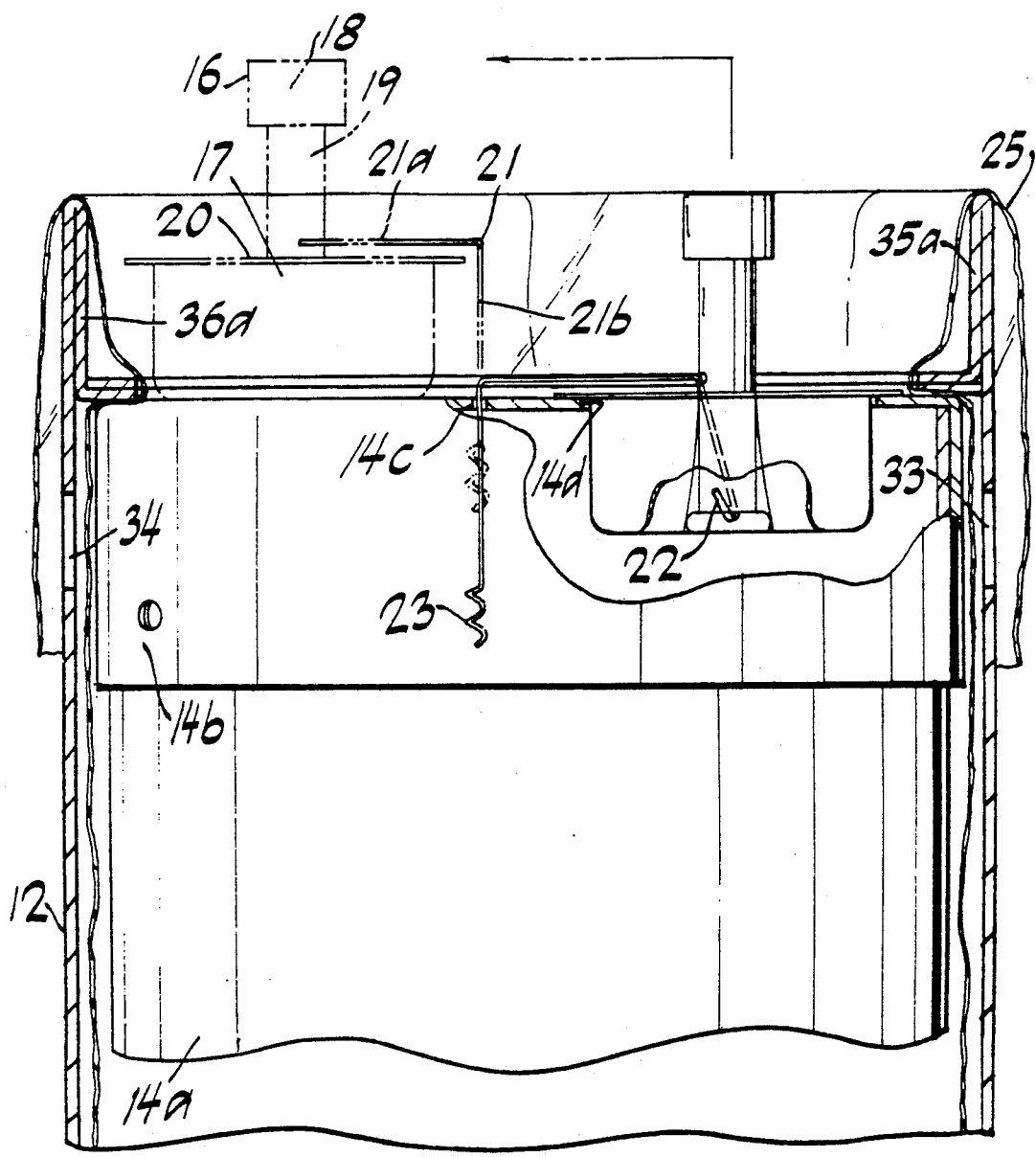
FIG. 2 is a partial side view of the apparatus of FIG. 1 showing operation of the stopper plug component of the invention.
Figure 2A:
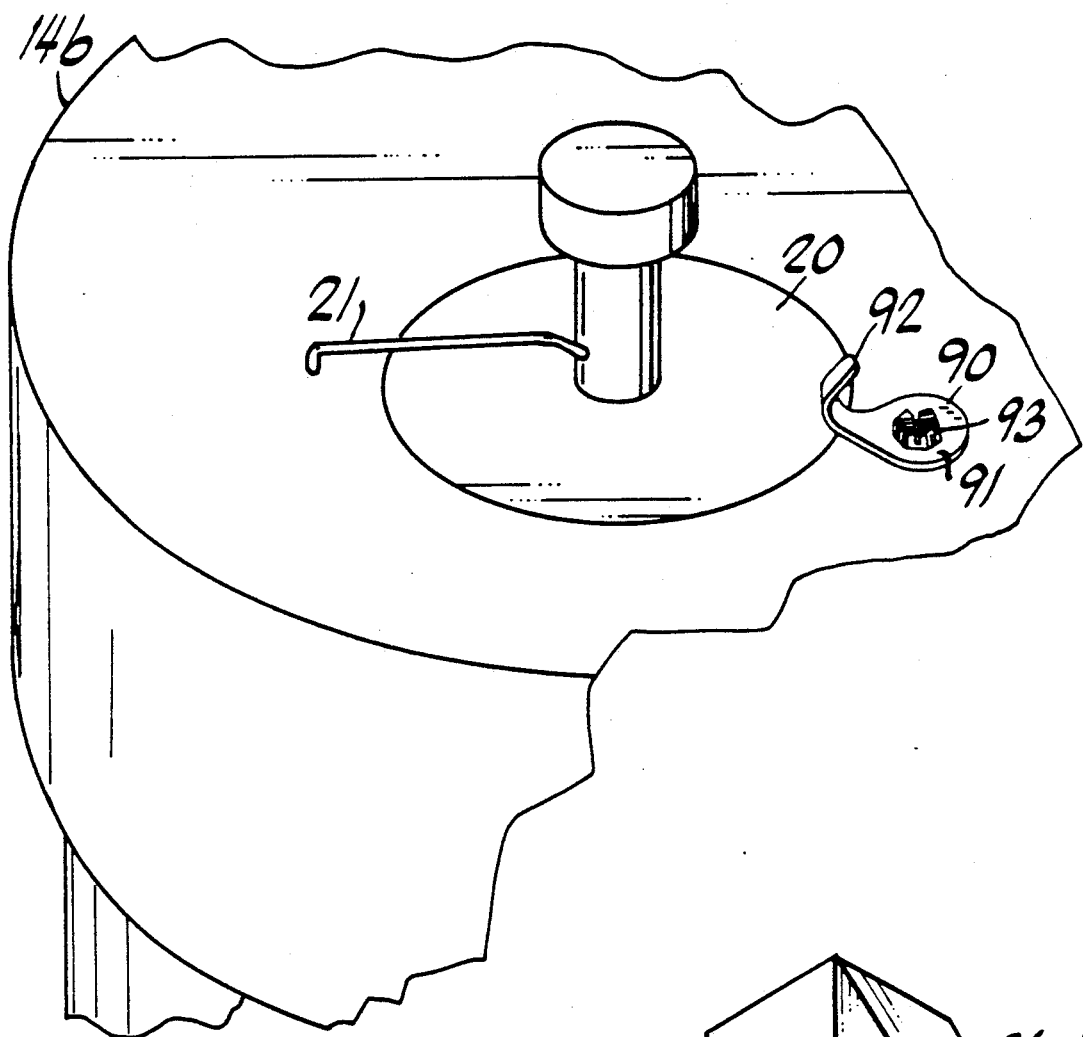
FIG. 2A is a partial isometric view of the stopper plug of FIG. 2 showing the plug securement member of the invention.
Figure 4A:
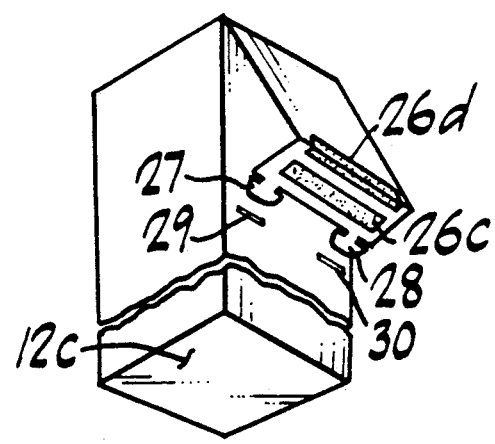
FIG. 4A is an isometric view showing the back side apparatus of FIG. 1.

To deposit and collect the used syringes within container 14 after the needles have been removed therefrom, the present invention provides a plug device 16 insertable within an opening 14d formed in container cover 14b. As preferably embodied, plug 16 comprises a plug body 17 providing a flange member 20, a shaft member 19 connected to the plug body, and a knob 18 connected to the shaft member, all formed from a substantially rigid molded plastic material. As shown in FIG. 2, when plug 16 is inserted into opening 14d, flange 20, which is generally wider than opening 14d, acts as a stop to prevent the plug from falling into the container. Plug 16 can be removed from opening 14b and placed on top of cover 14b so that used syringes which have been removed from their respective needle elements can be deposited into the container through opening 14d. As preferably embodied, opening 14b is dimensioned to a diameter of about 3⅜" so as to easily accommodate any size syringe device, as well as other used medical implements such as scalpels and the like, and to facilitate a person's ability to easily recognize when the container is filled to its intended capacity.

When plug 16 is inserted into opening 14d, the top of knob 18 is even with the top of housing 12, thus enabling the housing to be closed. When plug 16 is placed on top of cover 14b, the top of knob 18 is higher than the top of housing 12, which will prevent the housing from being closed. This insures that the user of the apparatus 10 will insert plug 16 into opening 14d before closing and transporting the housing. Advantageously, the present invention provides means for preventing plug 16 from inadvertently being detached from container 14. According to the invention, plug member 16 is provided with a generally L-shaped retaining wire 21 having a first leg member 21a connected to shaft 19 via hooked end portion 22, and a second leg member 21b formed with a cork-screw-like end portion 23 at the free end thereof. End portion 23 is inserted into container 14 via a small eyelet opening 14e formed in cover 14b. As here embodied, the L-shaped configuration of wire 21 allows plug 16 to pivot about opening 14b when removed therefrom, while the cork-screw configuration of end portion 23 prevents the wire from being removed from opening 14e while the plug is being handled by the user.

As here embodied, plug member 16 is provided with a clip member 90 to securely retain the plug within opening 14d formed in cover 14b. As preferably embodied, clip member 90 comprises a base member 91 pivotally connected to cover 14b via screw 93 (or other suitable fastener), and an integral finger member 92. According to the invention, by grasping finger 92 and urging it to the right or left, clip member 90 can be pivoted about screw 93. To secure plug 16 within cover opening 14d, the clip is pivoted so that finger 92 engages flange 20. The engaging surface of finger 92 is positioned relative to flange 20 so as to frictionally engage, and thereby bear upon, the flange to hold plug member 16 in place. When plug member 16 is to be removed from opening 14d, clip 90 is pivoted via finger 92 so as to disengage the finger from flange 20.

Because housing 12 and container 14 are, as preferably embodied, respectively constructed from paperboard and fibreboard materials, they are not leakproof. Accordingly, the present invention provides means for insuring that residual liquid that may remain in a used needle or syringe deposited in container 14 does not leak through the container and the housing. As here embodied, container 14 is placed in a plastic bag 25 prior to placement of the container within housing 12. Preferably, bag 25 should made from a polyethylene material having a thickness of about 3 one-thousanths of an inch.

Figure 3:
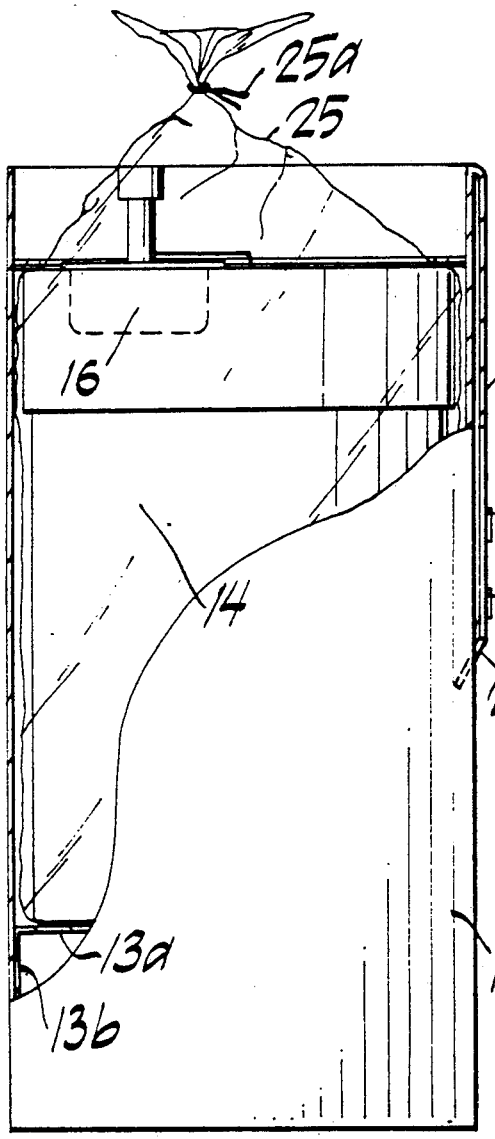
FIGS. 3 and 4 are partial side views of the apparatus of FIG. 1 showing operation of the plastic bag component of the invention.
Figure 4:
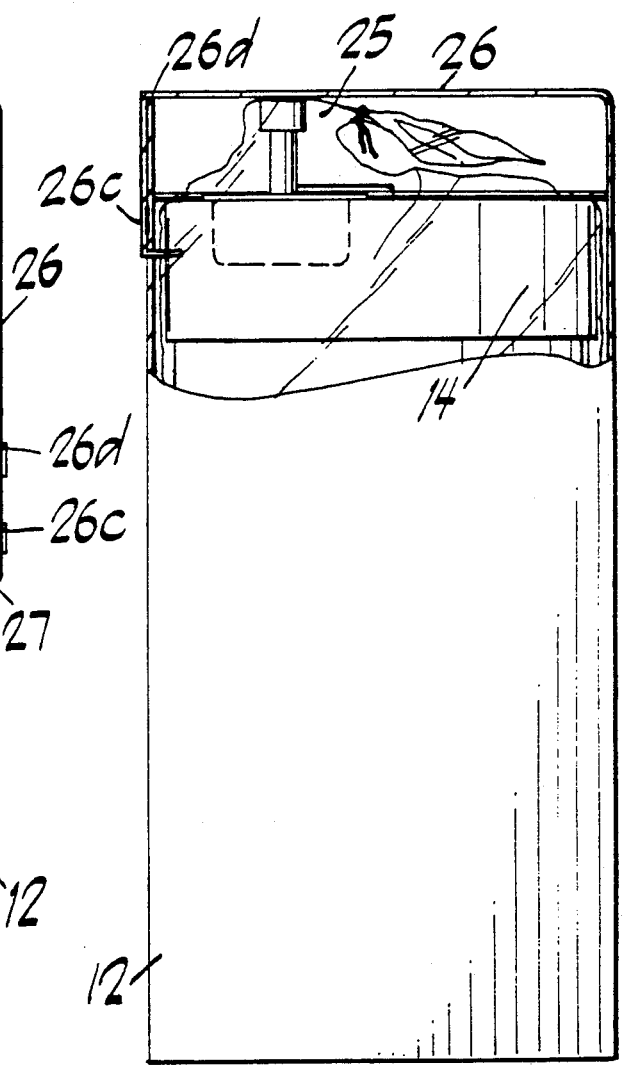

When apparatus 10 is in use, cover 26 of housing 12 is folded back and tabs 27 and 28 are inserted into slots 29 and 30 on housing sidewall 12d. The open end of bag 25 is pulled through the openings in protective flaps 35, 36 and draped over the top of sidewalls 12a–12d and a portion of cover 26 (see FIG. 1). Preferably, bag 25 should be long enough so that the portions folded over the housing sidewalls cover slots 31 and 32 and handles 33 and 34. As shown in FIGS. 3 and 4, when apparatus 10 is ready to be transported to disposal, the portions of bag 25 overlapping sidewalls 12a–12d are gathered up and tied together to close the bag, preferably with a standard twist-tie device as illustrated in the drawings by reference numeral 25a. Cover 26 can then be secured closed over the housing by removing tabs 27 and 28 from slots 29 and 30, folding the cover over opening 12f, inserting tabs 27 and 28 into slots 31 and 32 in sidewall 12a, and pressing adhesive strip 26c and 26d against sidewall 12a.

It will be appreciated by those skilled in the art that the present invention in its broader aspects is not limited to the particular embodiments shown and described herein, and that variations may be made which are within the scope of the accompanying claims without departing from the principle of the invention and without sacrificing its chief advantages.

What is claimed is:

1. An apparatus for safely disassembling hypodermic needle/syringe assemblies and collecting and storing the used needle and syringe implements for transport to disposal, comprising:
   a transport housing having sidewall means forming an opening therewithin, said housing providing a cover member adapted to releasably close said opening;
   a storage container disposed within said housing, said container having first entry means for receiving disassembled needle implements and second entry means for receiving disassembled syringe devices;
   plastic bag means surrounding said container; and a needle removal device affixed to said container in communication with said first entry means, said needle removal device adapted to engage the needle hub of a hypodermic needle which is threadably engaged to a syringe body so as to permit said syringe body to be rotatingly threadably disengaged from said needle and said needle to be deposited into said container via said first entry means.

2. The apparatus according to claim 1, wherein said cover member is hingingly connected to said sidewall means and formed with a flap member hingingly connected to said cover member and providing a pair of bendable tab members, said cover member and flap member pivotable about their corresponding hinge connections to allow said tab members to be bendably frictionally inserted within a first pair of tab engaging slots formed in said sidewall means to secure said cover member closed over said housing opening.

3. The apparatus according to claim 2, wherein said cover member is further formed with adhesive strip means on the underside thereof pressingly engagable with said sidewall means to further secure said cover member closed over said housing opening.

4. The apparatus according to claim 3, wherein said sidewall means is further formed with a second pair of tab engaging slots disposed at a generally opposite end of said housing opening from said first pair of tab engaging slots, said cover member and flap member pivotable about their corresponding hinge connections so as to permit said tab members to be bendably frictionally inserted into said second pair of tab engaging slots, thereby maintaining said housing in an open condition.

5. The apparatus according to claim 1, wherein said bag means is proportioned to be draped over at least a portion of said sidewall means.

6. The apparatus according to claim 5, wherein said bag means has a wall thickness of at least about 3 one-thousands of an inch.

7. The apparatus according to claim 1, wherein said second entry means is provided with plug means releasably retained therewithin to securely close said second entry means.

8. The apparatus according to claim 7, wherein said plug mean comprises:
a plug body member slidably insertable within said second entry means, said plug body member providing flange means proportioned to prevent said plug means from dropping through said second entry means into said container;
a shaft member connected substantially in perpendicular with said plug body member and providing a gripping knob member at the free end thereof; and
a generally L-shaped retaining wire member providing a first leg connected to said shaft member and a second leg entering said container through a hole formed therein, said second leg member formed with a cork-screw-like end portion disposed within said container and adapted to substantially prevent said second leg member from being removed from said hole.

9. The apparatus according to claim 1, wherein said needle removal device comprises:
a plate member affixed to said container and providing first receiving slot means;
a needle engaging member formed integrally with said base member in communication with said first entry means, said needle engaging member comprising a pair of opposed finger members integrated with a base portion to define second slot means disposed generally opposite said first slot means in lateral alignment therewith and at a generally lower elevation with respect thereto, said second slot means providing a receiving slot portion adjacent said first slot means and a contiguous engaging slot portion;
said needle hub member slidably translatable through said receiving slot portion into engagement with said device at said engaging slot portion such that said syringe body may be rotatingly threadably detached from said hub member, said unthreaded needle and syringe translatable out of said engaging slot portion, through said receiving slot portion, thence into said first receiving slot means such that said hub member is disposed below said plate member permitting said needle to drop into said container through said first entry means, said hub member engagable with the underside of said plate member in response to upward pulling forces applied to said syringe body to ensure complete detachment of said needle and syringe body.

10. The apparatus according to claim 9, wherein said plate member and needle engaging member are fabricated from an injection-molded thermoplastic material.

11. The apparatus according to claim 9, wherein said plate member and needle engaging member are fabricated from a metal alloy.

12. The apparatus according to claim 9, wherein said needle engaging member is canted downwardly with respect to said plate member.

13. The apparatus according to claim 9, wherein said needle engaging member is recessed into said plate member substantially in parallel therewith via a continuous sidewall member connecting said plate member to said needle engaging member.

14. The apparatus according to claim 9, wherein said first slot means has a generally U-shaped configuration.

15. The apparatus according to claim 14, wherein said receiving slot portion of said second slot means has a generally rectangular configuration.

16. The apparatus according to claim 15, wherein said engaging slot portion of said second slot means has a generally U-shaped configuration.

17. The apparatus according to claim 1, wherein said housing is fabricated from a corrugated paperboard material.

18. The apparatus according to claim 1, wherein said container is fabricated from a substantially rigid fibreboard material.

19. An apparatus for safely disassembling hypodermic needle/syringe assemblies and collecting and storing the used needle and syringe implements for transport to disposal, comprising:
a transport housing having sidewall means forming an opening therewithin, said housing providing a cover member hingingly connected to said sidewall means and formed with a flap member hingingly connected to said cover member and providing a pair of bendable tab members, said cover member and flap member pivotable about their corresponding hinge connections to allow said tab members to be bendably frictionally inserted within a first pair of tab engaging slots formed in said sidewall means to secure said cover member closed over said housing opening;
a storage container disposed within said housing, said container fabricated from a substantially rigid fibreboard material, said container having first entry means for receiving disassembled needle implements and second entry means for receiving disassembled syringe devices;

plastic bag means surrounding said container and proportioned to be draped over at least a portion of said sidewall means; and a needle removal device fabricated from an injection-molded thermoplastic material, comprising:

a plate member affixed to said container and providing first receiving slot means;

a needle engaging member formed integrally with said base member in communication with said first entry means, said needle engaging member comprising a pair of opposed finger members integrated with a base portion to define second slot means disposed generally opposite said first slot means in lateral alignment therewith and at a generally lower elevation with respect thereto, said second slot means providing a receiving slot portion adjacent said first slot means and a contiguous engaging slot portion;

said needle hub member slidably translatable through said receiving slot portion into engagement with said needle removal device at said engaging slot portion such that said syringe body may be rotatingly threadably detached from said hub member, said unthreaded needle and syringe translatable out of said engaging slot portion, through said receiving slot portion, thence into said first receiving slot means such that said hub member is disposed below said plate member permitting said needle to drop into said container through said first entry means, said hub member engagable with the underside of said plate member in response to upward pulling forces applied to said syringe body to ensure complete detachment of said needle and syringe body.

20. The apparatus according to claim 19, wherein said needle engaging member is canted downwardly with respect to said plate member.

21. The apparatus according to claim 19, wherein said needle engaging member is recessed into said plate member substantially in parallel therewith via a continuous sidewall member connecting said plate member to said needle engaging member.

22. The apparatus according to claim 19, wherein said first slot means has a generally U-shaped configuration.

23. The apparatus according to claim 22, wherein said receiving slot portion of said second slot means has a generally rectangular configuration.

24. The apparatus according to claim 23, wherein said engaging slot portion of said second slot means has a generally U-shaped configuration.

25. The apparatus according to claim 19, wherein said housing is fabricated from a corrugated paperboard material.

26. The apparatus according to claim 19, wherein said cover member is further formed with adhesive strip means on the underside thereof pressingly engagable with said sidewall means to further secure said cover member closed over said housing opening.

27. The apparatus according to claim 26, wherein said sidewall means is further formed with a second pair of tab engaging slots disposed at a generally opposite end of said housing opening from said first pair of tab engaging slots, said cover member and flap member pivotable about their corresponding hinge connections so as to permit said tab members to be bendably frictionally inserted into said second pair of tab engaging slots, thereby maintaining said housing in an open condition.

28. The apparatus according to claim 19, wherein said bag means has a wall thickness of at least about 3 one-thousands of an inch.

29. The apparatus according to claim 19, wherein said second entry means is provided with plug means releasably retained therewithin to securely close said second entry means.

30. The apparatus according to claim 29, wherein said plug means comprises:

a plug body member slidably insertable within said second entry means, said plug body member providing flange means proportioned to prevent said plug means from dropping through said second entry means into said container;

a shaft member connected substantially in perpendicular with said plug body member and providing a gripping knob member at the free end thereof; and a generally L-shaped retaining wire member providing a first leg connected to said shaft member and a second leg entering said container through a hole formed therein, said second leg member formed with a cork-screw-like end portion disposed within said container and adapted to substantially prevent said second leg member from being removed from said hole.

31. The apparatus according to claim 30, wherein said plug means further comprises a clip member pivotally connected to said container adjacent said flange means, said clip member formed with a finger member engagable with said flange means to secure said plug body within said second entry means.

* * * * *

UNITED STATES PATENT AND TRADEMARK OFFICE
CERTIFICATE OF CORRECTION

PATENT NO. : 5,031,767

DATED : July 16, 1991

INVENTOR(S) : John Bruno

It is certified that error appears in the above-identified patent and that said Letters Patent is hereby corrected as shown below:

Column 8, line 8, after "32," insert --respectively, formed on sidewall 12a of the housing, to secure--

Signed and Sealed this

First Day of December, 1992

Attest:

DOUGLAS B. COMER

*Attesting Officer*      *Acting Commissioner of Patents and Trademarks*